United States Patent [19]

Meurtin

[11] Patent Number: 5,016,266
[45] Date of Patent: May 14, 1991

[54] PROCESS AND APPARATUS FOR MONITORING MONOCRYSTALLINE STRUCTURES WITH IMAGES OF KIKUCHI PSEUDO-LINES

[75] Inventor: Michel Meurtin, Mazeres-Lezons, France

[73] Assignee: Turbomeca, Bordes, France

[21] Appl. No.: 482,791

[22] Filed: Feb. 21, 1990

[30] Foreign Application Priority Data

Feb. 24, 1989 [FR] France .................. 89 02409

[51] Int. Cl.⁵ .................. G01N 23/00; G01N 23/207; G01N 23/04; G21K 1/06
[52] U.S. Cl. .................................. 378/73; 378/84; 378/87; 378/62; 250/206; 250/307
[58] Field of Search .................. 378/73, 84, 87, 90, 378/92, 63, 62, 80; 250/399, 379, 310, 306, 307

[56] References Cited

U.S. PATENT DOCUMENTS 4,788,702 11/1988 Howe et al. .................. 378/73

Primary Examiner—Edward P. Westin
Assistant Examiner—Don Wong
Attorney, Agent, or Firm—Martin Smolowitz

[57] ABSTRACT

An object (12) is irradiated by means of a divergent and polychromatic beam of X-rays for producing a diagram composed of Kikuchi pseudo-lines. An X-ray generator (4) is mounted on a stand (1), and an automatic handler (13) presents the objects (12) in confronting relation to the microfocus (F) of the generator. An intensity amplifier (6) and a video camera (7) record the obtained diagrams composed of the pseudo-lines. The handler apparatus is controlled by an electronic device (17).

15 Claims, 3 Drawing Sheets

PROCESS AND APPARATUS FOR MONITORING MONOCRYSTALLINE STRUCTURES WITH IMAGES OF KIKUCHI PSEUDO-LINES

BACKGROUND OF THE INVENTION

The present invention relates to a process and an apparatus for detecting the presence of defects in monocrystalline structures.

The process which is at present most widely employed for effecting a quality control on monocrystalline structures is the LAUE process. Processes are also known employing a macro and micrographic observation.

The LAUE process on the other hand is a long and costly process requiring a preparation and use of point "shots" on the object to be examined, these "shots" covering only a very small area of about 1 sq. mm and consequently requiring to be multiplied a large number of times at many different angles, without however covering the whole of the surface area of the object, so that there subsists a wide margin of uncertainty while only the crystallographic orientation is given.

The applicant has found that it is possible to determine the crystallographic quality of monocrystalline structures by a rational exploitation of diagrams composed of Kikuchi pseudo-lines. However, the known present process for obtaining Kikuchi pseudo-lines consists in bombarding a monocrystalline structure placed in a vacuum with a beam of electrons, these lines appearing in the electronic microscope. This vacuum pressure process consequently cannot be practically used with objects of large dimensions having a monocrystalline structure, such as for example turbine blades.

SUMMARY OF THE INVENTION

The invention therefore has for principal objects to provide:
  a process for obtaining an image of Kikuchi pseudo-lines of a monocrystalline structure in an ambient atmosphere;
  a process for controlling by means of said process the crystallographic quality of objects of large dimensions having monocrystalline structures;
  an apparatus for carrying out the aforementioned processes for producing Kikuchi pseudo-lines and controlling the quality of monocrystalline structures of objects of large dimensions.

The invention therefore provides a process for obtaining an image of the Kikuchi pseudo-lines of a monocrystalline structure, comprising bombarding said monocrystalline structure with a beam of photons in a natural ambient atmosphere. The photons striking the monocrystals of the structure produce electrons which bounce on the reticular planes and thereby produce the Kikuchi pseudo-lines.

According to another feature of the invention, the monocrystalline structure is irradiated with a divergent polychromatic beam of X-rays.

According to a further feature of the invention, an X-ray generator of known type having a directional or panoramic microfocus is employed for irradiating said structure. Advantageously, the diameter of said microfocus is at the most 100 $\mu$m. Owing to the fact that it takes place in a free ambient atmosphere, this process may be carried out on objects of large dimensions.

Therefore, the invention also provides a process for monitoring and controlling the crystallographic quality of objects of large dimensions having a monocrystalline structure, comprising producing an enlarged picture of a diagram composed of Kikuchi pseudo-lines obtained by carrying out the aforementioned process, and analyzing said pseudo-lines. Advantageously, a video recording of the image of the diagram is effected and the image is processed by a computer with the use of an appropriate programme.

The invention also provides an apparatus for carrying out said processes, comprising a stand on which are mounted an X-ray generator having a microfocus, an assembly comprising in series an intensity amplifier, a video shooting apparatus, and an object support interposed between the microfocus and said amplifier.

According to one embodiment, the apparatus further comprises a movable support slidable in a direction perpendicular to the optical axis of said assembly and adapted to present an image receiver in confronting relation thereto.

Preferably, the apparatus further comprises means for presenting automatically and in succession the objects to be examined in facing relation to said microfocus.

The image receiver may be a fluorescent screen or a radiographic film.

DESCRIPTION OF THE DRAWINGS

The following description, with reference to the accompanying drawings given as non-limitative examples, will explain how the invention can be carried out.

DESCRIPTION OF THE PREFERRED EMBODIMENTS

Figure 1:
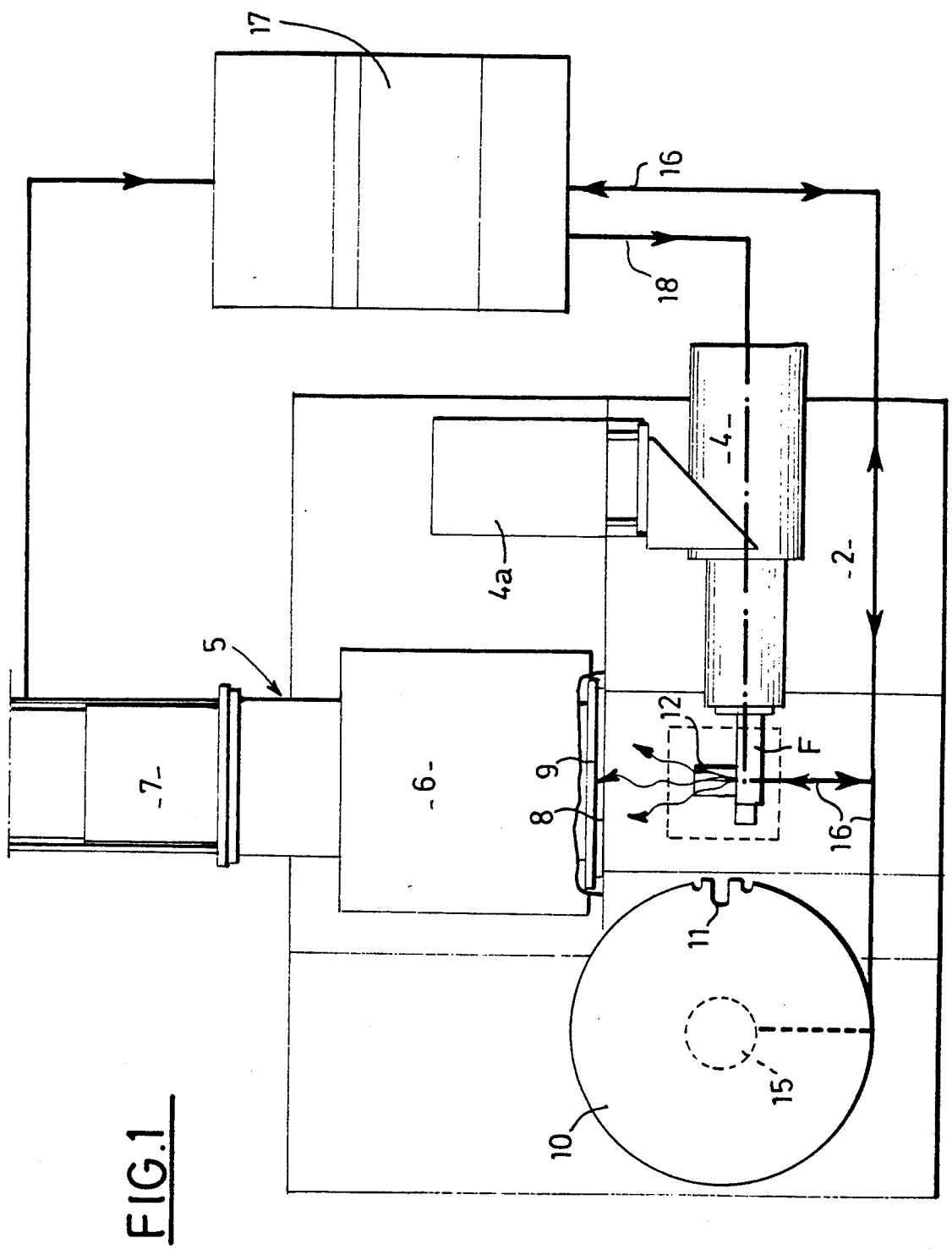
FIG. 1 is a diagrammatic plan view of the apparatus for carrying out the process according to the invention.
Figure 2:
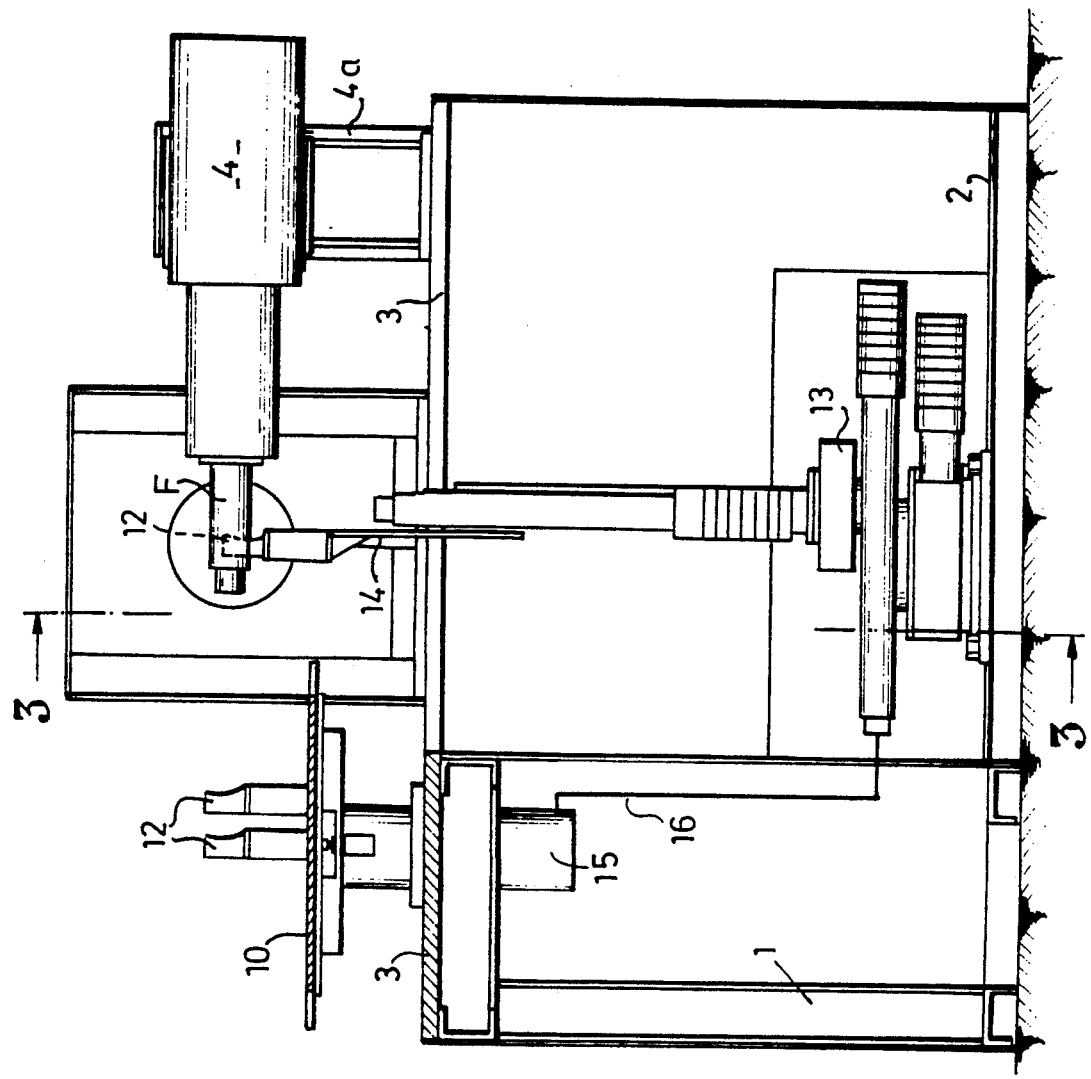
FIG. 2 is a diagrammatic side elevational view thereof.
Figure 3:
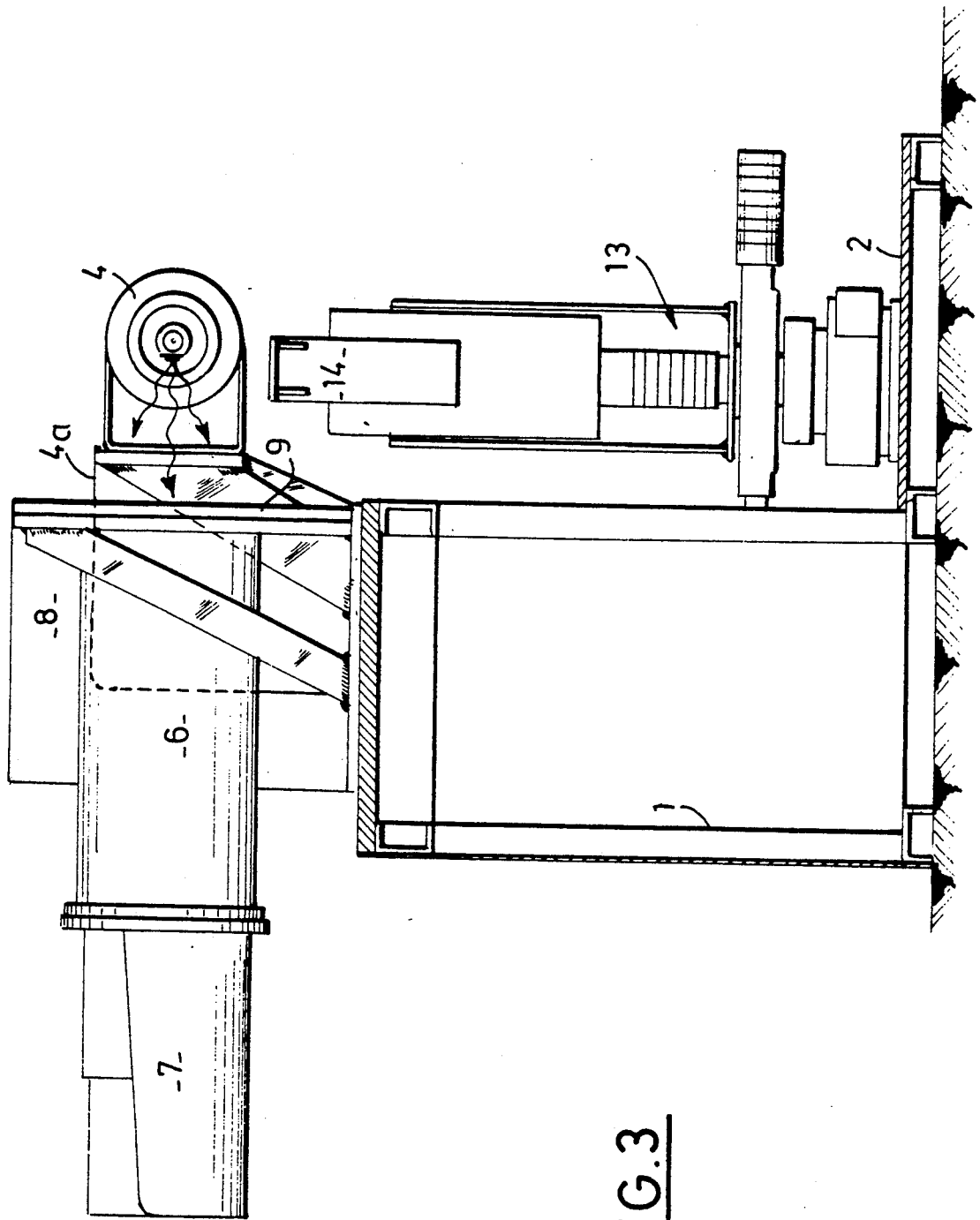
FIG. 3 is a sectional view taken on line 3—3 of FIG. 2.

According to one embodiment, the apparatus for carrying out the processes according to the invention comprises a stand 1 having a base 2 carrying an L-shaped table 3.

Mounted on one of the branches of the table 3 by means of a support 4a is an X-ray generator 4 of the industrial type, comprising a microfocus F having a diameter which is smaller than or equal to 100 $\mu$m, emitting a polychromatic radiation having a maximum energy of between 10 and 160 KeV with a tungsten anticathode.

Disposed on the same branch of the table 3 in confronting relation to the microfocus F is an assembly generally designated by the reference number 5 and comprising, in starting at the microfocus F, an intensity amplifier 6 and a video camera device 7 which are axialy aligned so as to provide an optical axis and also aligned with said microfocus F.

Disposed in front of the amplifier 6 is a laterally or vertically slidable support 8 adapted to receive a fluorescent screen 9 and permitting the interposition of the screen 9 between the amplifier 6 and the focus F.

Mounted on the other branch of the table 3 is a rotary plate 10 capable of being indexed and including on its periphery means 11 adapted to receive in a detachable manner objects 12 whose crystallographic quality must be checked or controlled, for example turbine blades having a monocrystalline structure.

An automatic apparatus 13 of known type, for example a handler, is mounted on the base 2 below the gap between the microfocus F and the amplifier 6. This handling apparatus comprises means 14 capable of seizing the objects 12 on the periphery of the plate 10, transferring them to a position in confronting relation to the microfocus F, orienting them and thereafter putting them back in position in the means 11 of the plate. Such a handling apparatus is well known in the art and will therefore not be described in more detail.

Means, such as a step-by-step motor 15, are provided for indexing the plate 10 angularly by bringing the means 11 of the plate in succession in alignment with the means 14 of the handler. The motor 15 is connected to the handler 13 and to an electronic driving and control device 17 through a conductor 16, the device 17 being itself connected to the generator 4 through a conductor 18.

The apparatus according to the invention operates in the following manner:

The objects to be checked or controlled, for example turbine blades 12, are disposed in the means 11 of the indexable plate 10.

The electronic drive device 17 actuates the handler 13, which takes an object 12 and brings it into a predetermined fixed position in confronting relation to the microfocus F.

The screen 9 is brought in confronting relation to the amplifier 6 and the generator 4 is supplied with power.

The photons emitted by the generator 4 strike the crystals of the microcrystalline structure of the object 12 and are diffracted in such manner that they cause to appear on the screen 9 the image of a diagram composed of Kikuchi pseudo-lines.

The operator observes the image on the screen 9, then the handler 13 orients the object at a different angle and the operator observes the new image.

The operator evaluates the images and, if he detects no defects, he withdraws the screen 9 and actuates the assembly 5 for recording the images of the diagrams which may be subsequently processed by a computer for a precise exploitation of the Kikuchi pseudo-lines by means of appropriate software.

The process and the apparatus according to the invention permit advantageously obtaining a diffracted radiographic image of the whole of the profile of the object exposed to the radiation of the generator, i.e. an overall image in contrast to the conventional spot techniques.

Furthermore, the results obtained are independent of the geometry of the profile of the examined part and in particular of its curvature, which is of particular interest in the case of turbine blades, and permits reducing to about 3 minutes at the most the time required for quality controlling a turbine blade.

What is claimed is:

1. Process for monitoring and controlling the crystallographic quality of objects having a monocrystalline structure, said process comprising bombarding said monocrystalline structure with a beam of photons in a natural ambient atmosphere, and producing an enlarged picture of a diagram composed of Kikuchi pseudo-lines obtained by bombarding said monocrystalline structure.

2. Process according to claim 1, including irradiating the monocrystalline structure with a divergent polychromatic beam of X-rays.

3. Process according to claim 2, including employing for irradiating said structure an X-ray generator having a microfocus selected from the group consisting of a directional microfocus and a panoramic microfocus.

4. Process according to claim 3, wherein said microfocus has a diameter not exceeding 100 $\mu$m.

5. Process according to claim 1, including effecting a video recording of the image of the diagram and processing the image by a computer with the aid of an appropriate program.

6. Apparatus for carrying out a process for controlling the crystallographic quality of objects having a monocrystalline structure, said apparatus comprising a detecting means for producing an enlarged picture of a diagram composed of Kikuchi pseudo-lines obtained by bombarding said monocrystalline structure with a beam of photons in a natural ambient atmosphere, said apparatus further comprising a stand, an X-ray generator having a microfocus, an assembly comprising in series an intensity amplifier, a video camera device, and an object support interposed between the microfocus and the intensify amplifier.

7. Apparatus according to claim 6, further comprising a computer and an appropriate program for effecting a video recording of the image of the diagram comprised of Kikuchi pseudo-lines and for processing the image by the computer with the aid of the appropriate program.

8. Apparatus according to claim 6, wherein said assembly has an optical axis, said apparatus further comprising a movable support slidable in a direction perpendicular to the optical axis of said assembly, an image receiver carried by said movable support, said movable support being adapted to present the image receiver in confronting relation to said assembly.

9. Apparatus according to claim 7, wherein said assembly has an optical axis, said apparatus further comprising a movable support slidable in a direction perpendicular to the optical axis of said assembly, an image receiver carried by said movable support, said movable support being adapted to present the image receiver in confronting relation to said assembly.

10. Apparatus according to claim 6, further comprising means for presenting said objects automatically and in succession in confronting relation to said microfocus.

11. Apparatus according to claim 7, further comprising means for presenting said objects automatically and in succession in confronting relation to said microfocus.

12. Apparatus according to claim 8, further comprising means for presenting said objects automatically and in succession in confronting relation to said microfocus.

13. Apparatus according to claim 9, further comprising means for presenting said objects automatically and in succession in confronting relation to said microfocus.

14. Apparatus according to claim 8, wherein said image receiver is a fluorescent screen.

15. Apparatus according to claim 8, wherein said image receiver is a radiographic film.

* * * * *